United States Patent
Wang et al.

(10) Patent No.: US 9,274,075 B2
(45) Date of Patent: Mar. 1, 2016

(54) PROXIMITY SENSOR DETECTING METALLIC AND NON-METALLIC OBJECTS

(71) Applicant: Mitsubishi Electric Research Laboratories, Inc., Cambridge, MA (US)

(72) Inventors: Bingnan Wang, Belmont, MA (US); Jiang Long, La Jolla, CA (US); Koon Hoo Teo, Lexington, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 71 days.

(21) Appl. No.: 14/168,506

(22) Filed: Jan. 30, 2014

(65) Prior Publication Data

US 2015/0212033 A1    Jul. 30, 2015

(51) Int. Cl.
*G01V 3/10* (2006.01)
*G01N 27/22* (2006.01)
*H03K 17/95* (2006.01)
*H03K 17/955* (2006.01)

(52) U.S. Cl.
CPC .............. *G01N 27/228* (2013.01); *G01V 3/101* (2013.01); *H03K 17/954* (2013.01); *H03K 17/955* (2013.01)

(58) Field of Classification Search
USPC ......... 324/682, 633, 652, 655, 668, 675, 708, 324/601, 705, 300, 322, 647; 340/686.6; 327/517
See application file for complete search history.

(56) References Cited

U.S. PATENT DOCUMENTS

| | | | |
|---|---|---|---|
| 4,859,931 A | | 8/1989 | Yamashita et al. |
| 4,950,987 A | | 8/1990 | Vranish et al. |
| 5,012,206 A | * | 4/1991 | Tigges ............................ 331/65 |
| 5,519,317 A | * | 5/1996 | Guichard et al. ............. 324/236 |
| 6,107,924 A | | 8/2000 | Kasai et al. |
| 6,801,044 B2 | | 10/2004 | Kesil et al. |

(Continued)

FOREIGN PATENT DOCUMENTS

| | | | |
|---|---|---|---|
| GB | 2 296 973 A | 7/1996 | |
| WO | WO 8700933 A1 * | 2/1987 | ..................... 324/329 |

OTHER PUBLICATIONS

Florian Von Detten, Daniel Basten, Alireza Ajami, "Low-cost Proximity Sensor System using Metamaterial Structures" Jan. 2013; In proceeding of: 17th International Conference on Electrical Engineering, Electronics and Instrumentation, Poster 2013, May 16, 2013. Prague.

(Continued)

*Primary Examiner* — Melissa Koval
*Assistant Examiner* — Nasima Monsur
(74) *Attorney, Agent, or Firm* — Dirk Brinkman; Gene Vinokur

(57) ABSTRACT

A method determines a type of an object in a proximity to a resonant structure having a resonant frequency as a metallic object if the object changes a phase of a power signal reflected by the resonant structure at frequencies below and above the resonant frequency. Otherwise, the method determines the type of the object as a non-metallic object.

6 Claims, 8 Drawing Sheets

(56) References Cited

U.S. PATENT DOCUMENTS

| | | | |
|---|---|---|---|
| 6,967,574 | B1 | 11/2005 | Nelson et al. |
| 6,972,575 | B2 | 12/2005 | Lambert et al. |
| 8,432,169 | B2 | 4/2013 | Niwa et al. |
| 8,975,900 | B2 * | 3/2015 | Poupyrev et al. ............ 324/633 |
| 2007/0001663 | A1 | 1/2007 | Hrubes et al. |
| 2007/0159185 | A1 | 7/2007 | Yang et al. |
| 2009/0051355 | A1 | 2/2009 | Yamakawa et al. |
| 2011/0152725 | A1 | 6/2011 | Demir et al. |
| 2013/0106769 | A1 | 5/2013 | Bakken et al. |

OTHER PUBLICATIONS

Ferran Martin, "Metamaterials for Wireless Communications, Radiofrequency, Identification, and Sensors." Review Article, Internationsl Scholarly Research Network, ISRN Electronics. vol. 2012. Article ID 780232.

Mam Yunis et al., Novel Planar Electromagnetic Sensors for Detection of Nitrates and Contamination in Natural Water Sources. IEEE Sensors Journal, vol. 11, No. 6, Jun. 2011.

* cited by examiner

PROXIMITY SENSOR DETECTING METALLIC AND NON-METALLIC OBJECTS

FIELD OF THE INVENTION

The invention relates generally to a proximity sensor, and more particularly to a proximity sensor for determining a type of an object in a proximity to the sensor.

BACKGROUND OF THE INVENTION

In the art of proximity sensing, there is a need to determine a type of an object, e.g., a metallic object or a non-metallic object, in a proximity to the sensor. Conventional sensors use a combination of the inductive and capacitive sensing to determine a type of detected object. Those sensors include at least two sensing units, which conduct capacitive sensing and inductive sensing respectively. This dual structure complicates the sensing system.

For example, U.S. 20070159185 describes security scanners with capacitance and magnetic sensor arrays. Similarly, U.S. Pat. No. 6,801,044 describes a system including a composite measuring unit composed of two identical and symmetrically arranged oscillation circuits with measurement elements in the form of identical and symmetrically arranged inductive coils and capacitor chips.

U.S. 20130106769 describes a mixed sensing method using alternate inductive and capacitive modes. The inductive mode and capacitive mode are realized by exciting the sensor in different modes. However, that method requires switching circuits, which reduces the detecting speed.

SUMMARY OF THE INVENTION

Some embodiments of an invention are based on a general recognition that when a source submit a signal to a structure, e.g., via a cable, a part of the signal is reflected by the structure back to the source, e.g., via the same cable. The parameters of the reflected signal depend on an impedance of the structure, and the impedance of the structure can be affected by another object in the proximity of the structure. Thus, a presence of the object in the proximity of the structure can affect the parameters of the reflected signal.

Specifically, an object in proximity of a resonant structure powered by a power signal can change the phases of the power signal reflected from the resonant structure. Moreover, the objects of different types, i.e., a metallic object or non-metallic object, change the phases of the power signal differently due to the differences in principles of inductive and capacitive coupling. Such difference can be detected on off-resonant frequencies of the power signal reflected from the resonant structure. Thus, the proximity sensor including a resonant structure can utilize not the resonant property of the structure, but its off-resonant properties for distinguishing metallic and non-metallic objects in proximity of the resonant structure.

For example, the metallic object in the proximity of the resonant structure having a resonant frequency can change the phase of the reflected signal on both types of the off-resonant frequencies, i.e., on the frequencies above the resonant frequency and on the frequencies below the resonant frequency. Conversely, the non-metallic object in the proximity of the resonant structure can change the phase of the power signal on frequencies of either above or below the resonant frequency, but not on both types of the off-resonant frequencies.

Therefore, by detecting the change of the phase of the power signal reflected from the resonant structure on both or just one type of the off-resonant frequencies, it is possible to distinguish between types of the object in proximity to the resonant structure.

Accordingly, one embodiment discloses a method for determining a type of an object in a proximity to a resonant structure having a resonant frequency. The method includes determining the type of the object as a metallic object if the object changes a phase of a power signal reflected by the resonant structure at frequencies below and above the resonant frequency; and otherwise determining the type of the object as a non-metallic object.

Another embodiment discloses a proximity sensor including a sensor unit having a resonant structure with a resonant frequency; a power source for supplying to the resonant structure a power signal including a first signal with a first off-resonant frequency and a second signal with a second off-resonant frequency selected such that a value of the resonant frequency is between values of the first and the second off-resonant frequencies; a detecting unit for detecting, if an object is in proximity to the sensor unit, one or both of a first change in a phase of the first signal and a second change in a phase of the second signal; and a processor for determining a type of the object as a metallic object if both the first and the second changes are detected, and for determining the type of the object as a non-metallic object only one of the first change and the second change is detected.

DETAILED DESCRIPTION OF THE PREFERRED EMBODIMENTS

Some embodiments of the invention are based on a realization that an object in proximity to a resonant structure powered by a power signal can change the phases of the power signal reflected from the resonant structure. The objects of different types, i.e., a metallic object or non-metallic object, change the phases of the power signal differently due to the differences in principles of inductive and capacitive coupling. Such difference can be detected on off-resonant frequencies of the power signal reflected from the resonant structure.

Some embodiments of art invention are based on a general recognition that when a source submit a signal to a structure, e.g., via a cable, a part of the signal is reflected by the structure back to the source, e.g., via the same cable. The parameters of the reflected signal depend on an impedance of the structure, and the impedance of the structure can be affected by another object in the proximity of the structure. Thus, a presence of the object in the proximity of the structure can affect the parameters of the reflected signal.

Specifically, an object in proximity of a resonant structure powered by a power signal can change the phases of the power signal reflected from the resonant structure. Moreover, the objects of different types, i.e., a metallic object or non-metallic object, change the phases of the power signal differently due to the differences in principles of inductive and capacitive coupling. Such difference can be detected on off-resonant frequencies of the power signal reflected from the resonant structure. Thus, the proximity sensor including a resonant structure can utilize not the resonant property of the structure, but its off-resonant properties for distinguishing metallic and non-metallic objects in proximity of the resonant structure.

Figure 1:
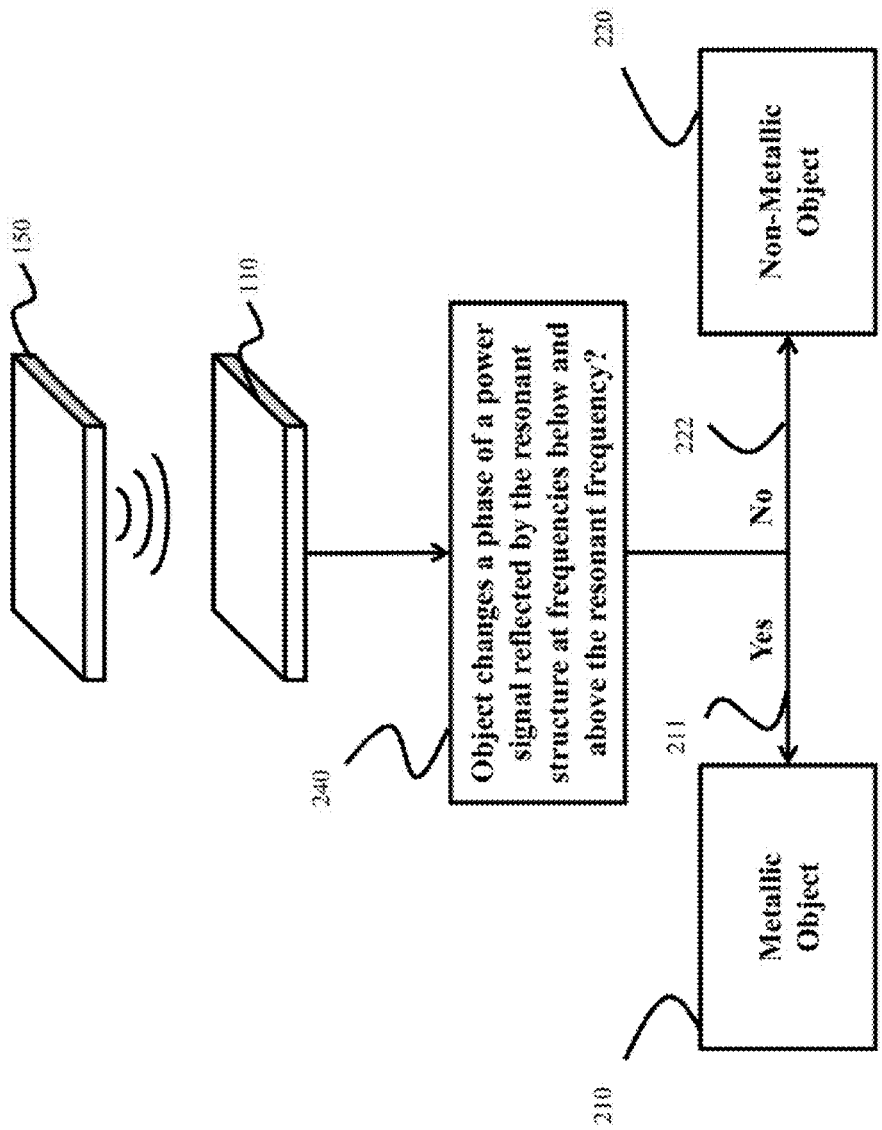
FIG. 1 is a schematic of a system and a method for determining a type of an object in a proximity to a resonant structure according to some embodiments of the invention.

FIG. 1 shows a schematic of a method and system for determining a type of an object 150 in proximity to a resonant structure 110 having a resonant frequency according to some embodiments of the invention. For example, the metallic object in the proximity of the resonant structure can change the phase of the reflected signal on both types of the off-resonant frequencies, i.e., on the frequencies above the resonant frequency and on the frequencies below the resonant frequency. Conversely, the non-metallic object in the proximity of the resonant structure can change the phase of the power signal on frequencies of either above or below the resonant frequency, but not on both types of the off-resonant frequencies.

Therefore, by detecting the change of the phase of the power signal reflected from the resonant structure on both or just one type of the off-resonant frequencies, it is possible to distinguish between metallic 210 and non-metallic 220 types of the object 150 in proximity to the resonant structure 110.

Accordingly, some embodiments of the invention determine 240 if the object 150 changes a phase of a power signal reflected by the resonant structure at frequencies below and above the resonant frequency. If yes 211, the type of the object is determined as metallic 210. If not 222, e.g., only the phase on one of the off-resonant frequency below or above the resonant frequency is changed, the type of the object is determined as non-metallic 220.

Therefore, by detecting the change of the phase of the power signal reflected from the resonant structure on both or just one type of the off-resonant frequencies, the embodiments can distinguish between types of the object approaching the resonant structure.

Figure 2:
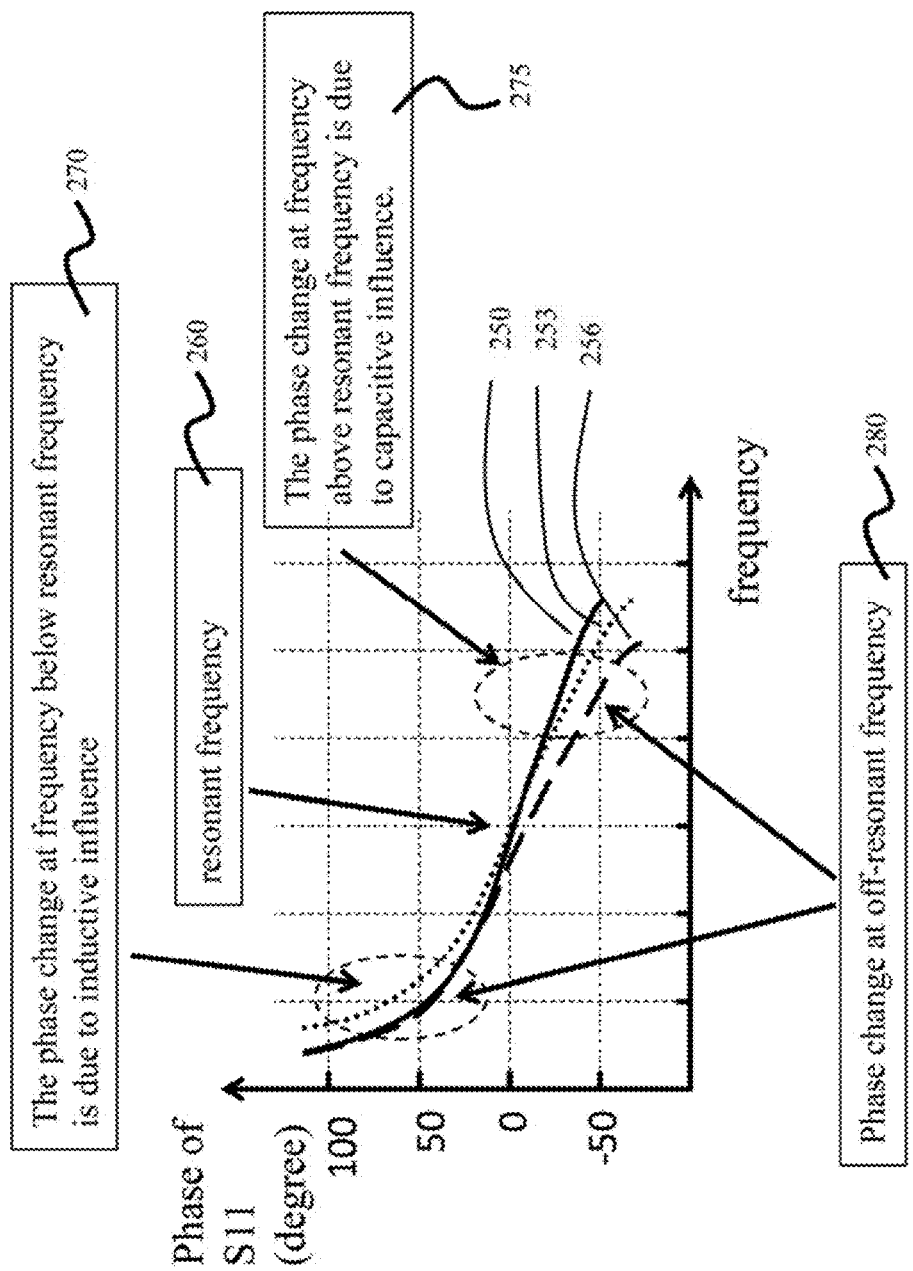
FIG. 2 is a graph showing a difference in phases of a reflected signal on different all-resonant frequencies.

FIG. 2 shows the difference in phase of the reflected power signal on resonant and off-resonant frequencies. The type of the object can be determined by comparing the phase change at both off-resonant frequencies.

In FIG. 2, the line 250 represents the phase of the reflected power signal without any object in the proximity of the resonant structure. The line 253 represents the phase of the reflected power signal when a metallic object is in the proximity to the resonant structure and the line 256 represents the phase of the reflected power signal when a non-metallic object is in the proximity to the resonant structure. The resonant frequency, 260 is the frequency where the phase of the reflected power signal crosses 0 degrees or 180 degrees.

The difference in phase change 280 is used to determine the type of the object. For example, the change 270 with respect the phase 250 is a phase change at frequency below the resonant frequency, which is due, e.g., to inductive coupling with a metallic object. The change 275 with respect the phase 250 is the phase change of the reflected power signal at frequency above the resonant frequency which is due, e.g., to a capacitive coupling with a metallic or a non-metallic objects.

Figure 3A:
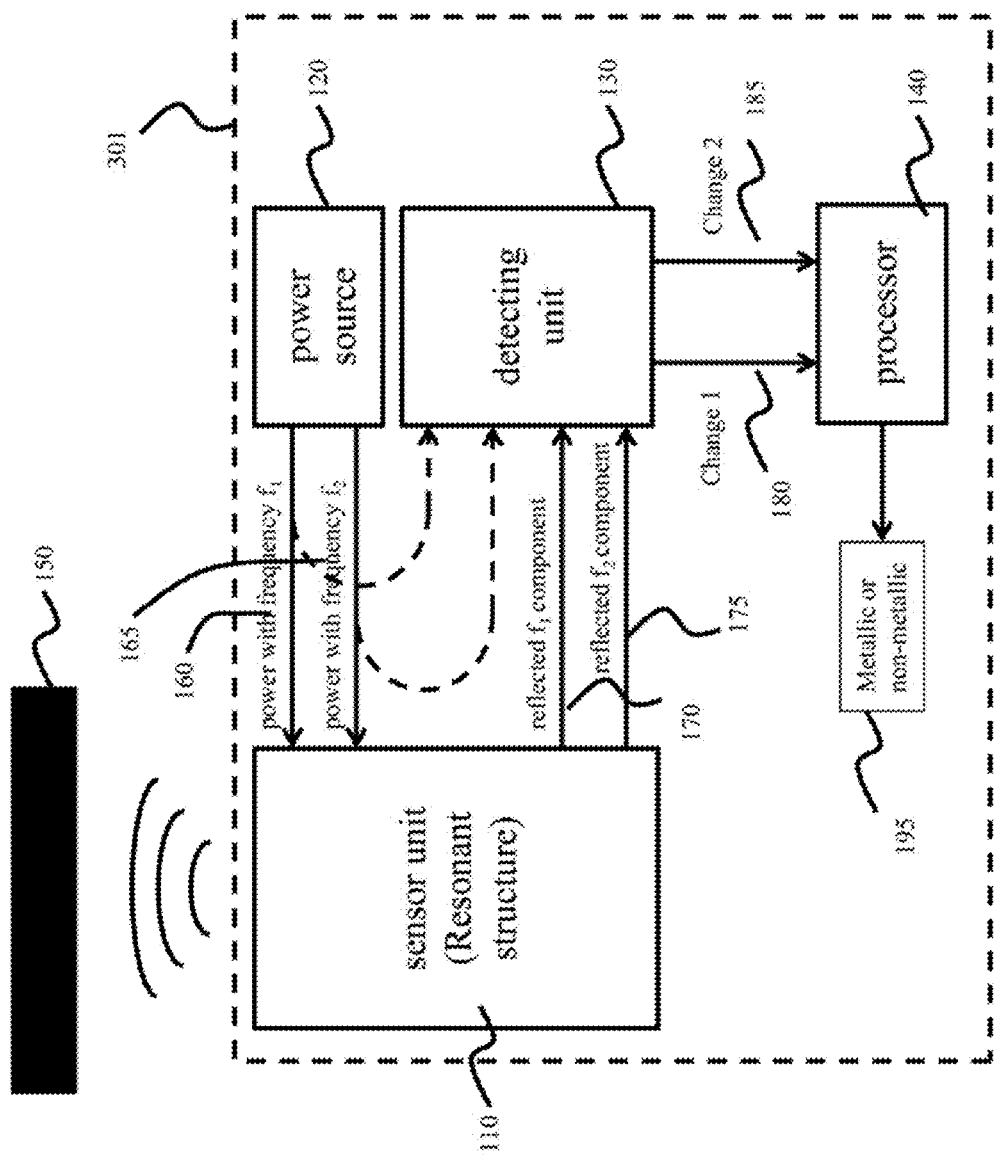
FIG. 3A is a block diagram of a proximity sensor according to some embodiments of the invention.
Figure 3B:
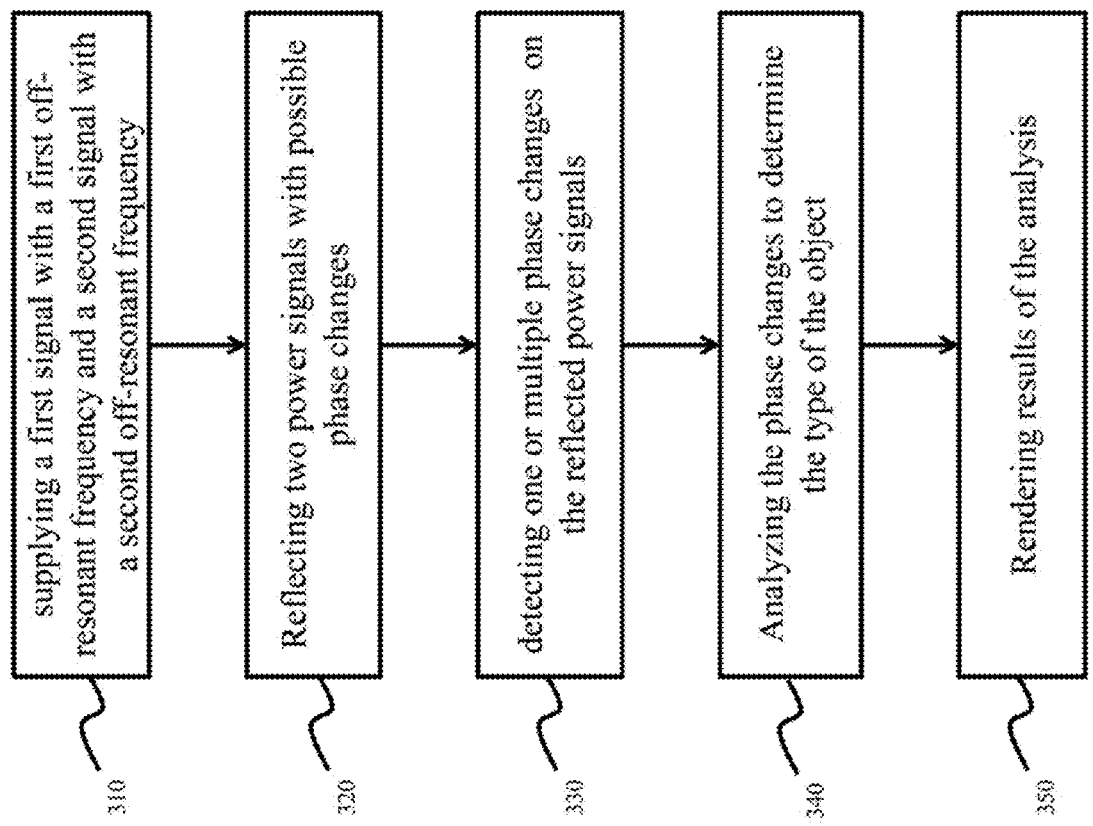
FIG. 3B is a flow chart of an exemplar operation of the proximity sensor of FIG. 3A.

FIGS. 3A and 3B show an example of a proximity sensor 301 and operations of the proximity sensor 301 according to some embodiments of the invention. The proximity sensor 310 includes a sensor unit 110, a power source 120, a detecting unit 130 and a processor 140. The sensor unit has a resonant structure with a resonant frequency that interacts with the object 150. The power source 120 supplies 310 a power signal to the resonant structure. The power signal can include a first signal 160 with a first off-resonant frequency and a second signal 165 with a second off-resonant frequency selected such that a value of the resonant frequency is between values of the first and the second off-resonant frequencies. For example, the first signal has the frequency below resonant frequency and the second signal has the frequency above the resonant frequency.

Both power signals are supplied to the sensor unit, for sensing an object in the proximity to the resonant structure, and to the detecting unit, for a reference. In one embodiment, the frequencies of the first and the second signals are selected within an inductive or capacitive region of the resonant frequency.

The two signals 160 and 165 are reflected 320 by the sensor unit 110 as a first reflected signal 170 corresponding to the frequency of the first signal 160, and as a second reflected signal 175 corresponding to the frequency of the second power signal 165.

The signals 160 and 165 and the reflected signals, 170 and 175, are detected 330 by the detecting unit, 130. The phases of the corresponding signals are compared to determine a first change 180 in a phase of the first signal and/or a second change 185 in a phase of the second signal. Values representing detected changes 180 and 185, are sent to the processor 140.

The processor analyzes 340 the change of the phase and determines the type 195 of object. For example, the processor determines a type of the object as a metallic object if both the first and the second changes are detected, and determines the type of the object as a non-metallic object only one of the first change and the second change is detected. In some embodiments, the result of the analysis are rendered 350, e.g., into a memory, on a display device, or submitted to another application. Examples of the applications include, but not limited to an automatic drilling machine control, automotive car seat occupation detection system, robotic arm/hand sensing, biosensing, factory automation, and security applications.

Figure 4:
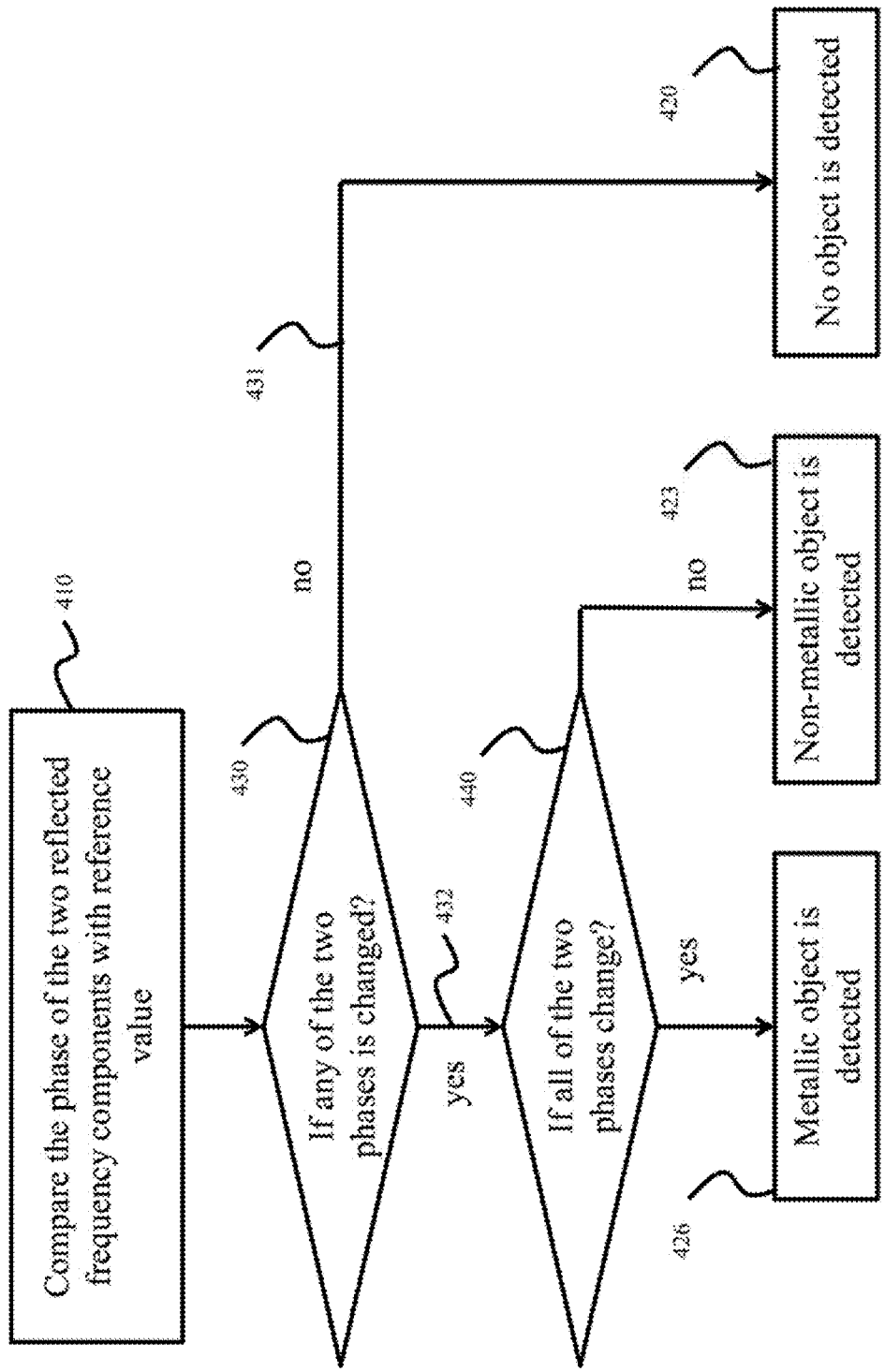
FIG. 4 is a flow chart of an exemplar operation of a processor of the proximity sensor of FIG. 3A.

FIG. 4 shows a flow chart of an exemplar operation of the processor 140 according to one embodiment. The processors determine if an object is in proximity to the resonant structure by comparing 410 the phase of the two reflected signals with the reference value of the phases of the original first and the second signals. The processor determines 430 if any of the first or the second change is present. For example, in one embodiment, the change is considered detected if the difference between the phases of corresponding supplied and reflected signals is above a threshold.

If the processor detects no changes 431 than there is no object 420 in the proximity to the resonant structure. If the processor detects 432 a first change of the phase of the power signal at a first off-resonant frequency than the object is in the proximity to the resonant structure, and the processor tests 440 for a second change of the phase of the power signal at a second off-resonant frequency. The processor determines the type of the object as the metallic object 426 if the second change is detected, and otherwise determines the type of the object as the non-metallic object 423.

The sensing of the proximity sensor operates at two off-resonant frequencies, of which one is above the resonant frequency and the other is below the resonant frequency. For a structure that only has a single resonance, the frequencies below and above the resonant frequency are easy to select. The frequencies above the resonant frequency are the frequencies larger than the target resonant frequency and the frequencies below the resonant frequency are the frequencies smaller than the target resonant frequency.

However, the resonant structure can have multiple resonant frequencies. Thus, some embodiments select the first and the second off-resonant frequencies, such that only one value of the resonant frequency is between the values of the first and the second off-resonant frequencies.

Figure 5:
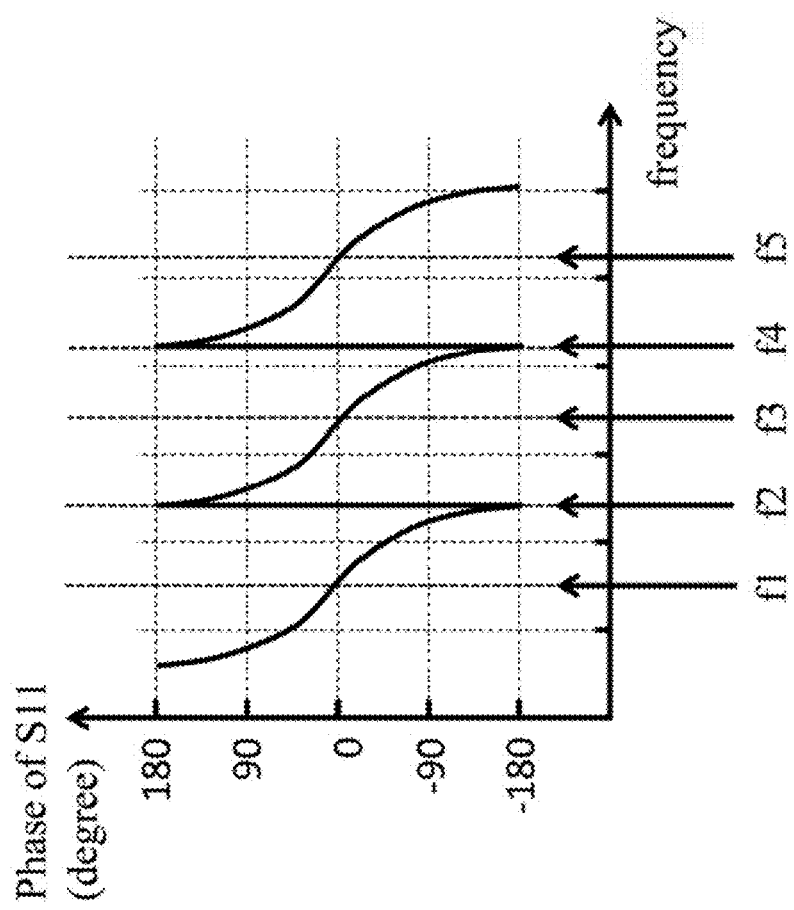
FIG. 5 a plot showing a selection of off-resonant frequency for a resonant structure with multi-resonant frequencies according to some embodiments of the invention.

FIG. 5 shows five resonant frequencies, f1 through f5, with f1<f2<f3<f4<f5. The frequencies are ordered from the smallest to the largest. The frequencies above the resonant frequency are the frequencies larger than the targeted resonant frequency, but smaller than the next resonant frequency. The frequencies below the resonant frequency are the frequencies smaller than the targeted resonant frequency, but larger than the previous resonant frequency, in that order.

If the frequency f3 is selected as the target resonant frequency for sensing the object, the frequencies above the resonant frequency are frequencies larger than f3, but smaller than f4. The frequencies below the resonant frequency are the frequencies smaller than f3, but greater than f2.

The shape and the dimension of the resonant structure impact the value of the resonant frequency. Some embodiments of the invention design various resonant structures to reduce the resonant frequency, which can reduce the cost of the sensor.

Figure 6:
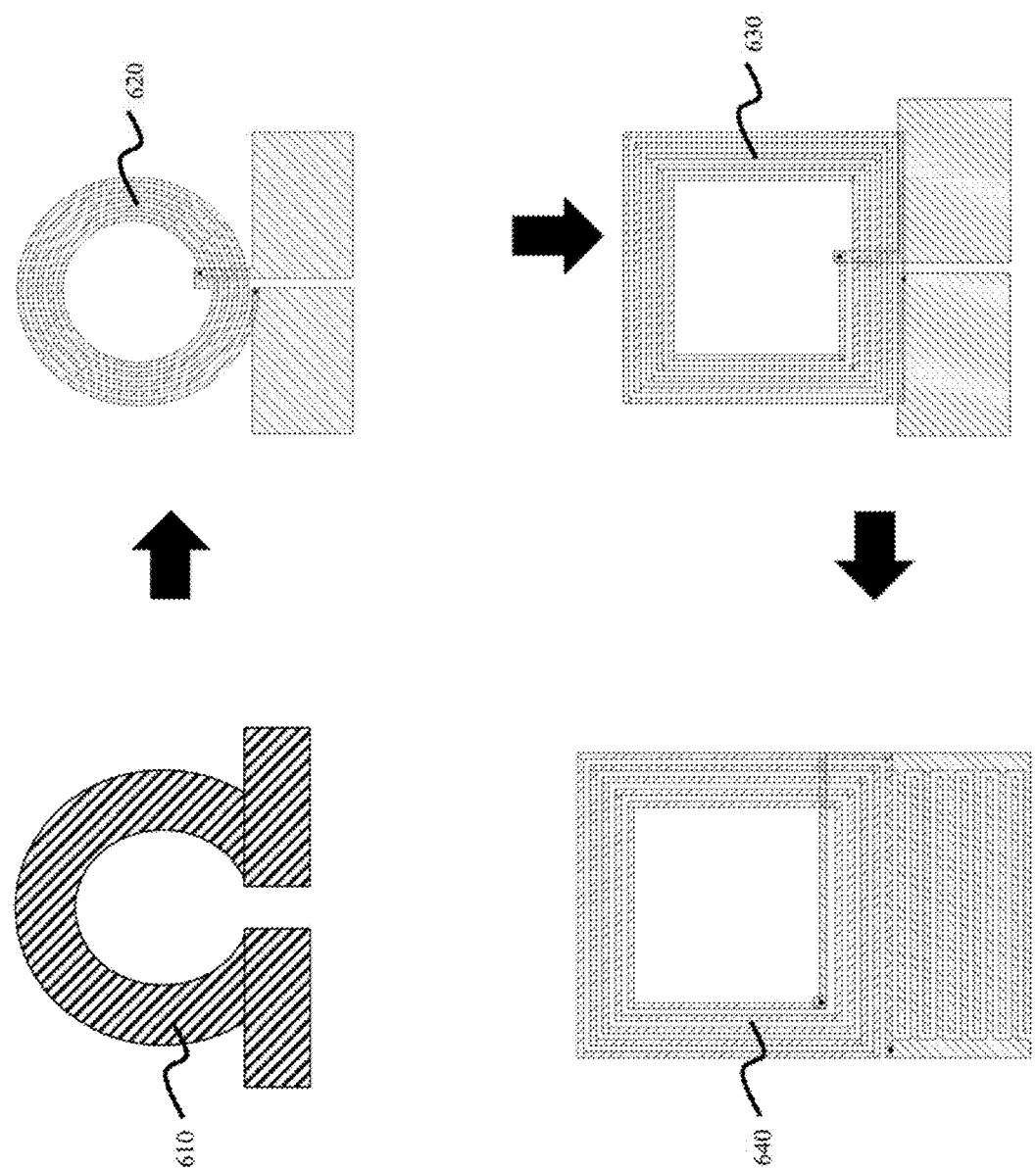
FIG. 6 is a comparison of different sensor designs adjusted to manipulate resonant frequency according to some embodiments of the invention.

FIG. 6 shows some examples of the resonant structure used by some embodiments. The structure 610 has an omega shape. The resonant frequency of the structure 610 can be reduced by reshaping the arc shape of the omega shape of the structure with a multi-turn circular spiral structure, 620. The circular spiral structure can be reshaped into a rectangular coil structure 630, to further reduce the resonant frequency. For further reduction of resonant frequency, the two parallel bars at the bottom can be replaced with an inter-digital structure 640.

Figure 7:
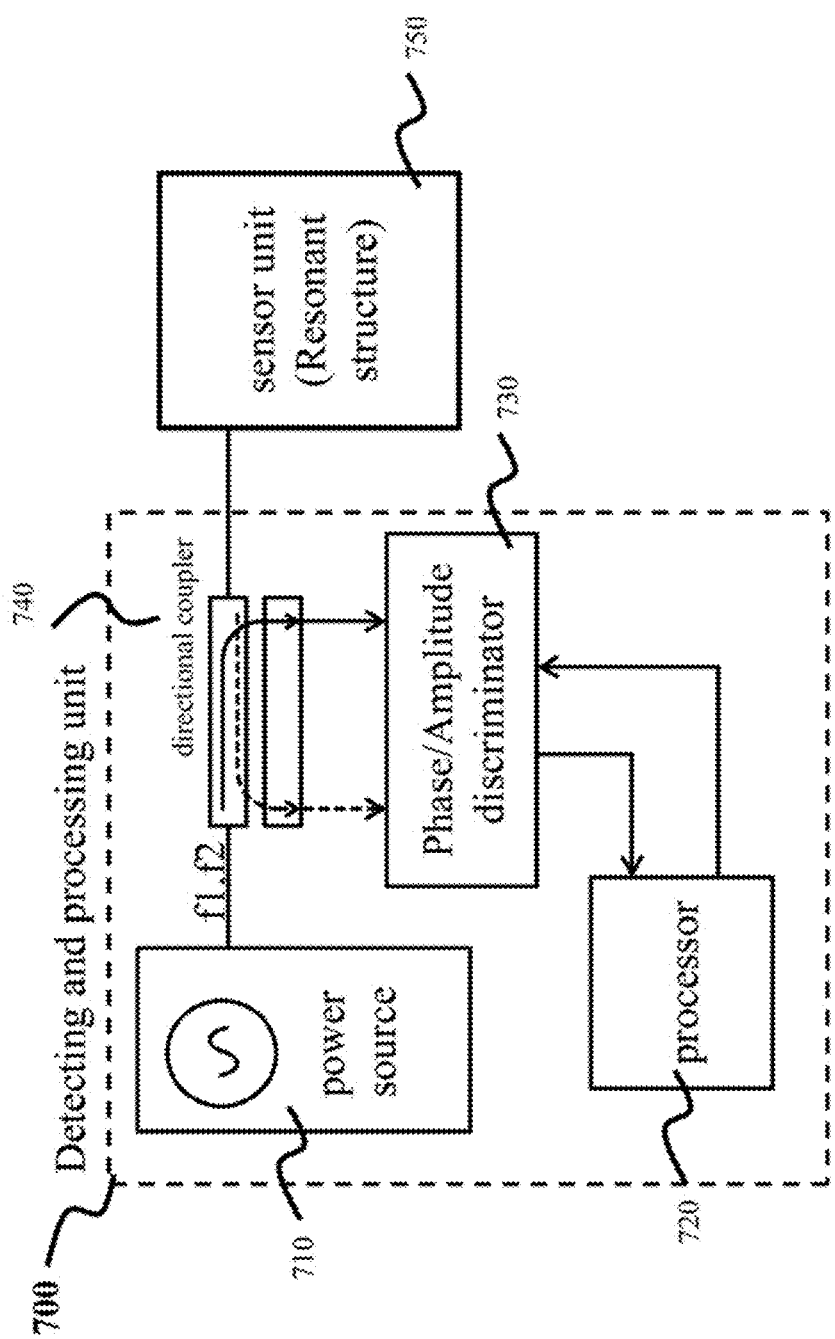
FIG. 7 is a block diagram of a detecting a processing unit according to some embodiments of the invention.

FIG. 7 is a block diagram of a detecting and processing unit 700 according to some embodiments of the invention. In one embodiment, the detecting and processing unit 700 is implemented using a vector network analyzer. Generally, a vector network analyzer measures both amplitude and phase properties. The detecting and processing unit of this embodiment includes a power source 710, a directional coupler 740, a phase and amplitude discriminator 730, and a processor 720. The resonant structure 750 is usually external to the unit.

In another embodiment, the sensing system includes a radio frequency integrated circuit (RFIC). The power source can be implemented with a dual frequency crystal oscillator, e.g., the Si532. Phase and amplitude discriminator can be implemented with AD8302, which is a fully integrated RFIC, used to measure amplitude and phase between input signals. A coupler can be implemented using various directional coupler design techniques.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format. The processor can be connected to memory, transceiver, and input/output interfaces as known in the art.

Also, the various methods or processes outlined herein may be coded as software that is executable on one or more processors that employ any one of a variety of operating systems or platforms. Alternatively or additionally, the invention may be embodied as a computer readable medium other than a computer-readable storage medium, such as signals.

The terms "program" or "software" are used herein in a generic sense to refer to any type of computer code or set of computer-executable instructions that can be employed to program a computer or other processor to implement various aspects of the present invention as discussed above.

Use of ordinal terms such as "first," "second," in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Although the invention has been described with reference to certain preferred embodiments, it is to be understood that various other adaptations and modifications can be made within the spirit and scope of the invention. Therefore, it is the object of the append claims to cover all such variations and modifications as come within the true spirit and scope of the invention.

We claim:

1. A method for determining a type of an object in a proximity to a resonant structure having a first resonant frequency, comprising:

supplying a power signal to the resonant structure, the power signal having frequency components at a first off-resonant frequency and a second off-resonant frequency within an inductive or a capacitive region of the resonant frequency, wherein a value of the resonant frequency is between values of the first and the second off-resonant frequencies, wherein the resonant structure has multiple resonant frequencies, and wherein the first and the second off-resonant frequencies are selected such that only one value of the first resonant frequency is between the values of the first and the second off-resonant frequencies;

determining the type of the object as a metallic object when the object changes a phase of a power signal reflected by the resonant structure at frequencies below and above the first resonant frequency, further comprising:

detecting a first change of the phase of the reflected power signal at a first off-resonant frequency;

testing for a second change of the phase of the reflected power signal at a second off-resonant frequency; and determining the type of the object as the metallic object when the second change is detected; and determining the type of the object as a non-metallic object when the second change is not detected.

2. The method of claim 1, wherein the testing comprises:

determining, at the second off-resonant frequency, a difference between the phase of the power signal supplied to the resonant structure and the phase of the power signal reflected by the resonant structure; and detecting the second change when the difference is above a threshold.

3. A proximity sensor, comprising:
a sensor unit having a resonant structure with multiple resonant frequencies including a first resonant frequency;
a power source for supplying to the resonant structure a power signal having frequencies including a first signal with a first off-resonant frequency and a second signal with a second off-resonant frequency within an inductive or a capacitive region of the resonant frequency, and wherein the first and the second off-resonant frequencies are selected such that only one value of the first resonant frequency is between values of the first and the second off-resonant frequencies;
a detecting unit for detecting, when an object is in proximity to the sensor unit, one or both of a first change in a phase of the first signal and a second change in a phase of the second signal, wherein the detecting unit detects the first change of the phase of the power signal at the first off-resonant frequency and tests for the second change of the phase of the power signal at the second off-resonant frequency; and
a processor for determining a type of the object as a metallic object when both the first and the second changes are detected, and for determining the type of the object as a non-metallic object when only one of the first change and the second change is detected.

4. The proximity sensor of claim 3, wherein the first and the second off-resonant frequencies are within an inductive or a capacitive region of the first resonant frequency.

5. The proximity sensor of claim 3, wherein the power source is supplying the power to the sensor unit over a transmission line, wherein the detecting unit includes a coupler connected to the transmission line for receiving the power signal supplied by the power source and a power signal reflected from the sensor unit.

6. The proximity sensor of claim 5, wherein the processor determines, at the first or the second off-resonant frequency, a difference between a phase of the power signal supplied to the resonant structure and a phase of the power signal reflected by the resonant structure and detects the first or the second change when the difference is above a threshold.

* * * * *